(12) United States Patent
Fee

(10) Patent No.: US 6,680,780 B1
(45) Date of Patent: Jan. 20, 2004

(54) INTERFEROMETRIC PROBE STABILIZATION RELATIVE TO SUBJECT MOVEMENT

(75) Inventor: Michale Sean Fee, New Vernon, NJ (US)

(73) Assignee: Agere Systems, Inc., Allentown, PA (US)

( * ) Notice: Subject to any disclaimer, the term of this patent is extended or adjusted under 35 U.S.C. 154(b) by 0 days.

(21) Appl. No.: 09/472,326

(22) Filed: Dec. 23, 1999

(51) Int. Cl.$^7$ ................................................ G01B 9/02
(52) U.S. Cl. ...................................... 356/498; 356/501
(58) Field of Search ................................. 356/477, 479, 356/482, 496, 498, 501, 505, 506, 507, 511

(56) References Cited

U.S. PATENT DOCUMENTS

| | | | |
|---|---|---|---|
| 4,139,304 A | * 2/1979 | Redman et al. | ............. 356/511 |
| 5,440,121 A | * 8/1995 | Yasutake et al. | ............. 250/306 |
| 6,191,862 B1 | * 2/2001 | Swanson et al. | ............. 356/450 |

* cited by examiner

*Primary Examiner*—Frank G. Font
*Assistant Examiner*—Andrew H. Lee
(74) *Attorney, Agent, or Firm*—Nancy R. Gamburd

(57) ABSTRACT

The present invention provides a method and system to actively stabilize a probe, such as a microelectrode, relative to movement of the subject, utilizing laser interferometry. In the preferred embodiments, a probe is mounted on a manipulator such that the probe moveable in response to a control voltage. A laser interferometer is utilized to transmit a first light beam to the subject and to receive a reflected light beam, to modulate a second light beam with a radio frequency signal to form a reference light beam, and to combine the reflected light beam and the reference beam to form an interference pattern. A demodulator is utilized to quadrature demodulate a phase shift of a radio frequency component of the interference pattern to determine a displacement signal representative of an amount and direction of subject movement, and to convert the displacement signal to the control voltage. The probe is then moved in response to the control voltage, providing stabilization relative to subject movement, and the probe may then be utilized for desired measurements within the subject.

28 Claims, 3 Drawing Sheets

$k = 2\pi/\lambda$ $\emptyset(t) = k\, x(t)$

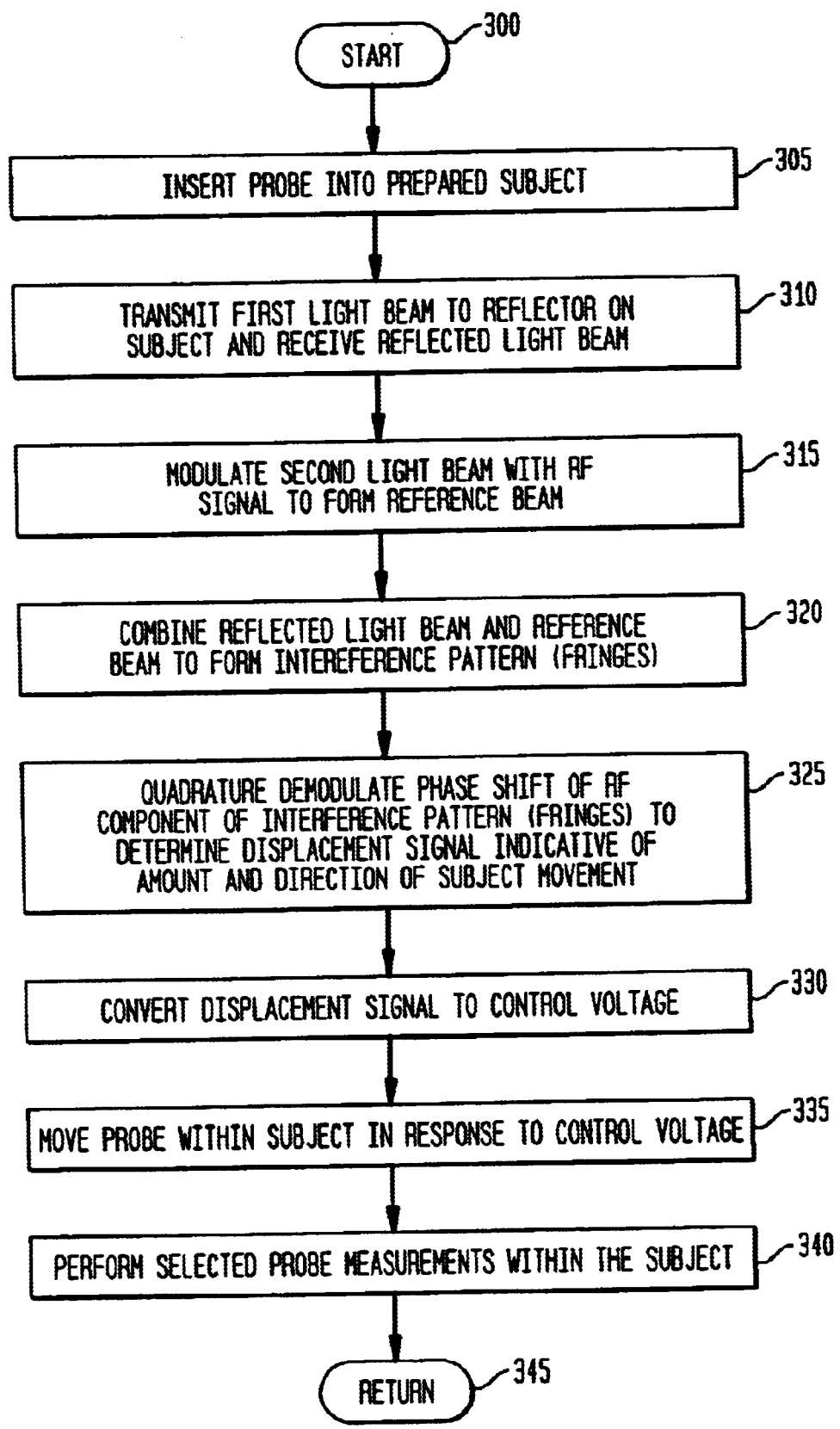

INTERFEROMETRIC PROBE STABILIZATION RELATIVE TO SUBJECT MOVEMENT

CROSS-REFERENCE TO RELATED APPLICATION

The present invention is related to Fee, U.S. Pat. No. 6,377,619, issued Apr. 23, 2003, entitled "Predictive Probe Stabilization Relative to Subject Movement", filed concurrently herewith and commonly assigned to Agere Systems, Inc. (formerly assigned to Lucent Technologies, Inc.), and incorporated by reference herein, with priority claimed for all commonly disclosed subject matter (the "related application").

1. Field of the Invention

The present invention relates, in general, to probe stabilization relative to movement of a subject. More particularly, the present invention relates to interferometric and active stabilization, of an intracellular probe, relative to the movement of the subject.

2. Background of the Invention

Much of our understanding of the function of the brain has come from probing the nervous system at the level of single neurons. With few exceptions, the study of single neurons in behaving animals has been limited to extracellular recordings of action potentials. Action potentials, however, represent only the final, output state of a neuron whose response is essentially determined by the electrical and chemical interactions between smaller, functionally distinct neuronal compartments such as synapses, dendrites, and somata. Nearly all experimental information about the properties and behavior of neurons at this level comes from in-vitro and cell culture experiments. Furthermore, it is known that neuronal integration and firing properties are modulated by neuromodulatory influences and other activities. As a consequence, complete understanding of brain function ultimately requires observation of neuronal compartments and their interactions in intact, live and behaving subject animals.

Problems with mechanical stability make observations of neurons much more difficult in whole-animal preparations than in in-vitro or cell culture preparations. Many structures of interest in neurons are small (on the order of 1 to 10 microns in size), and because electrical and optical probes must be positioned near or inside the cell membrane to function, high quality and long lasting recordings require stable mechanical placement of the probe relative to the tissue. Drift or motion of the electrode or other probe relative to the recorded cell may interfere with good probe penetrations or seals on a neuron. Even when good penetration or seal is achieved, motion may also cause large variations in the recorded signals, degrade the health of the cell, and limit the duration of the recording.

Although a number studies have been published that involve intracellular recordings in anesthetized animals and even awake animals, brain motion makes intracellular recording difficult under even the best conditions. In all these experiments, the essential means of stabilizing the brain is to restrain the head of the animal with a stainless steel plate or pin secured to the cranium, potentially interfering with desired measurements. For example, such restraining systems do not allow for measurements in an active, moving subject, thereby limiting experimental measurements to non-active physiological states. Other methods, such as passive tracking of an electrode, may damage fragile brain tissue, or interfere with the subject under study and potentially affect the resulting measurements.

As a consequence, a need remains to provide a method and system for probe stabilization, relative to subject movement, to provide for accurate measurement within a live subject. The method and system should be active, and should accommodate gross or large-scale subject movement which may otherwise interfere with accurate measurements. In addition, the method and system should not alter or interfere with the physiological states of the subject, and should otherwise minimize contact with the subject tissue, to avoid interfering with the processes under study, to avoid tissue damage, and also to avoid other potential sources of error.

SUMMARY OF THE INVENTION

In accordance with the present invention, a method and system are provided for active probe stabilization, for accommodating subject movement which may otherwise interfere with accurate measurements. In addition, the method and system of the present invention do not alter or interfere with the physiological states of the subject, and otherwise minimizes contact with the subject tissue, to avoid interfering with the processes under study, to avoid tissue damage, and also to avoid other potential sources of error.

In the preferred method and system for active probe stabilization, a probe (such as a microelectrode) is mounted on a piezoelectric manipulator and inserted into the subject, so that the probe is moveable in response to a control voltage. A laser interferometer is utilized to generate a light beam and to split the light beam into first and second light beams. The interferometer is operable to transmit the first light beam to the subject and to receive a reflected light beam. The interferometer modulates the second light beam with a modulating signal, such as a 110 MHz radio frequency signal, to form a reference light beam. The interferometer then combines the reflected light beam and the reference beam to form an interference pattern.

A demodulator is coupled to the manipulator and to the interferometer. The demodulator provides the control voltage to the manipulator for probe movement. Using the interference pattern detected within the interferometer, the demodulator quadrature demodulates a phase shift of the modulating signal (RF signal) to determine a displacement signal. The displacement signal is proportional to the amount and direction of subject movement, and may be in increments of one-fourth of a wavelength of the laser light beams. The displacement signal may accommodate comparatively significant subject movements, on the order of 30–40 microns. The displacement signal is then converted to an analog form as the control voltage input into the manipulator.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 3 is a flow diagram illustrating a method for interferometric probe stabilization relative to subject movement in accordance with the present invention.

DETAILED DESCRIPTION OF THE INVENTION

Figure 1:
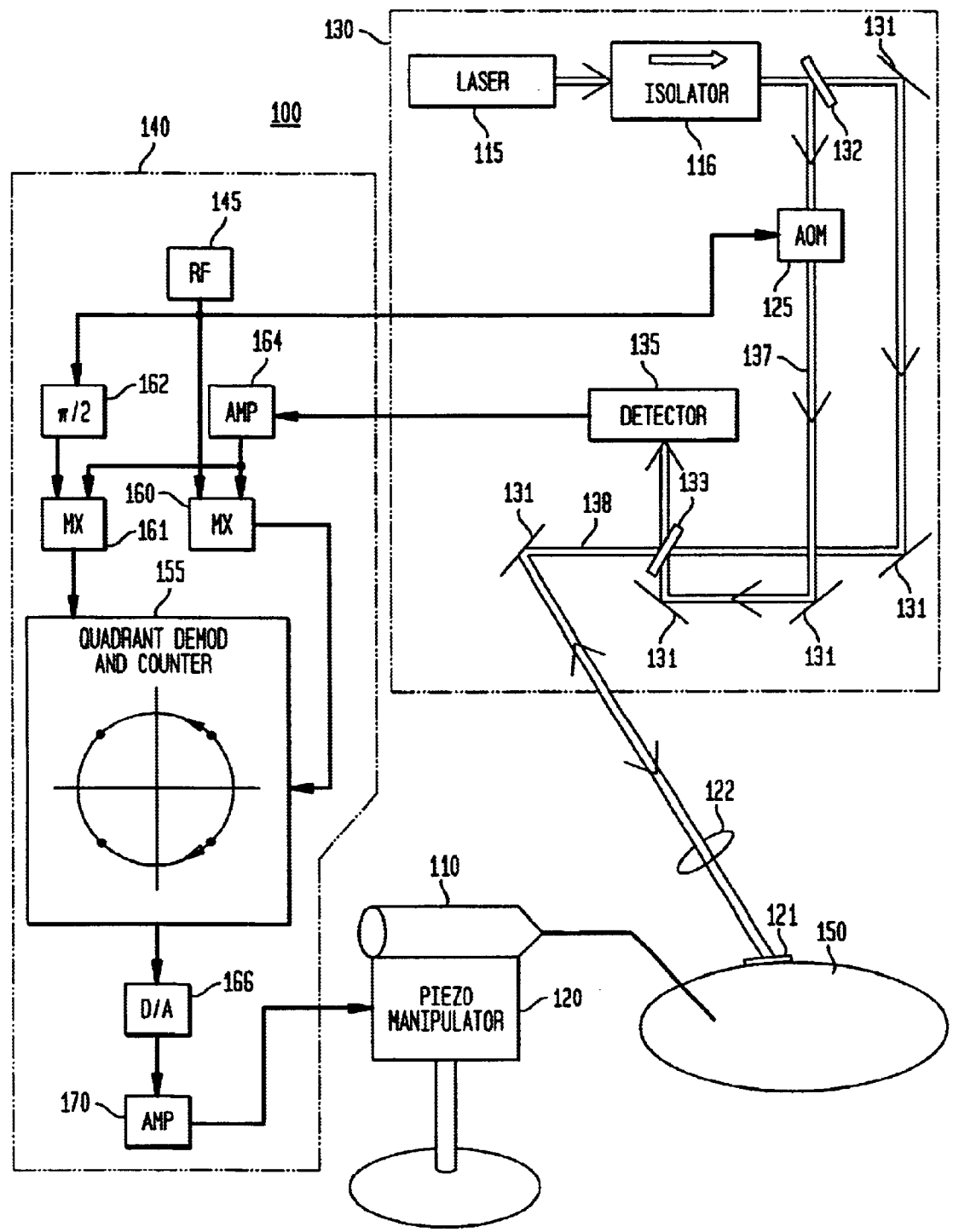
FIG. 1 is a block diagram illustrating a system for interferometric probe stabilization relative to subject movement in accordance with the present invention.

While the present invention is susceptible of embodiment in many different forms, there are shown in the drawings and will be described herein in detail specific embodiments thereof, with the understanding that the present disclosure is to be considered as an exemplification of the principles of the invention and is not intended to limit the invention to the specific embodiments illustrated.

As mentioned above, a need remains to provide a method and system for probe stabilization, relative to subject movement, to provide for accurate measurement within a live subject. In accordance with the present invention, a method and system are provided for active probe stabilization, accommodating and tracking comparatively gross or large-scale subject movement which may otherwise interfere with accurate measurements. In addition, the method and system of the present invention do not alter or interfere with the physiological states of the subject, and otherwise minimizes contact with the subject tissue, to avoid interfering with the processes under study, to avoid tissue damage, and also to avoid other potential sources of error.

FIG. 1 is a block diagram illustrating a system 100 for interferometric probe stabilization relative to subject 150 movement in accordance with the present invention. The system 100 includes an interferometer 130, a demodulator 140, and a probe 110 mounted or otherwise attached to a moveable piezoelectric manipulator (arm) 120. In the preferred embodiment, the piezoelectric manipulator 120 should have (generally) a linear response to a control voltage, which is input from the demodulator 140. The probe 110 is typically inserted into the subject 150 for desired measurements. In accordance with the present invention, the probe 110 is moved by or with the piezoelectric manipulator 120 in response to the control voltage which, in turn, is generated by the demodulator 140 based upon the tracking of any movement of the subject 150 using the interferometer 130. As used herein, the probe 110 may be any one or more of a wide variety of devices requiring stabilization to achieve its intended purpose. For example, the probe 110 may be an intracellular electrode (or microelectrode), with stabilization in accordance with the present invention for accurate intracellular recordings. In other embodiments, the probe 110 may be a surgical instrument, a microscopic instrument, a microscope (such as a two photon scanning laser microscope), a fiber optic scope, or any other device for which relative stabilization is necessary or desirable.

A significant empirical observation is also incorporated into the preferred embodiment of the present invention. Active mechanical stabilization of a probe 110, such as an intracellular recording electrode, typically requires two steps: (1) measuring or inferring the motion of tissue; and (2) moving the electrode in such a way as to precisely track the motion. Most generally, this requires continuous monitoring of the tissue position in all three spatial dimensions and a corresponding adjustment of the recording electrode in three dimensions. The fine microelectrodes that are commonly used for intracellular neuronal recording, however, are extremely laterally compliant at the tip. More specifically, the tip moves passively with the tissue if the displacement is not along the electrode axis. As a consequence, in accordance with the present invention, active tracking of the electrode position may be limited to tracking subject movement along the direction of the electrode axis, with the compliance of the tip passively accommodating lateral movement of the subject. Under other circumstances, however, such as use of other probe types, the methodology of the present invention may be utilized in all three spatial dimensions.

Continuing to refer to FIG. 1, the interferometer 130 of the system 100 may be of any type or kind known to those skilled in the art. In the preferred embodiment, the interferometer 130 consists of a laser 115 (preferably with an isolator 116), a plurality of mirrors 131, a splitter 132, a combiner 133, an acousto-optical modulator ("AOM") 125, and a detector 135. The detector 135 is typically comprised of a plurality of photodiodes. The splitter 132 and combiner 133 are typically prisms or other optical materials as known in the art. In other equivalent embodiments, the interferometer 130 also may be implemented utilizing fiber optics.

When the interferometer 130 is operative, i.e., powered on and functioning, a light beam from the laser 115 is split (by splitter 132) into two beams. One of the beams from the splitter 132 is further modulated (doppler shifted) by AOM 125 using a radio frequency ("RF") signal, preferably at 110 MHz, as a modulating signal generated by RF generator 145, to form a reference beam 137. Modulating signals at other frequencies may be used equivalently. The second beam from the splitter 132, referred to herein as measuring beam 138, is transmitted via various mirrors 131 and lens 122 to a reflector 121. The reflector 121, which also may be a mirror, is preferably mounted on or otherwise attached to the subject 150 in close proximity to the area of insertion of the probe 110. For example, in the preferred embodiment for measuring neurons, the reflector 121 is a small mirror mounted (such as with a surgical glue) to the cranium of the subject 150, adjacent to a craniotomy used for probe insertion. Equivalently, in lieu of reflector 121, light may be scattered directly from the subject 150 tissue. (Also equivalently, optical coherence tomography may be used to generate the displacement signal (discussed below)).

The measuring beam 138, as reflected from the reflector 121 on the subject 150, is combined with the reference beam 137 (by combiner 133) to form an interference pattern (such as interference fringes) at the detector 135. As discussed in greater detail below, with movement of the subject 150, corresponding changes in the interference pattern (beat noise of the RF signal) are detected and utilized for the probe 110 to track such movement (via demodulator 140 and manipulator 120). In particular, changes in the phase of the RF signal (110 MHz) are utilized to detect fringe movements in intervals of one-quarter wavelength ($\lambda/4$).

The signal from the detector 135 (which also may be amplified in amplifier 164), representing an interference pattern or fringes from the reference beam 137 and the reflected measuring beam 138, is demodulated in demodulator 140. The (amplified) signal from the detector 135 and the RF signal from the RF generator 145 are combined in mixer 160, generating a cosine function of the phase of the RF signal. The (amplified) signal from the detector 135, and the RF signal from the RF generator 145 having a ninety-degree ($\pi/2$) phase shift (from block 162), are combined in mixer 161, generating a sine function of the phase of the RF signal. These sine and cosine functions of the phase of the RF signal from the detector 135 are then quadrant demodulated, in increments of one-quarter wavelength ($\lambda/4$), with transitions accumulated and counted, in quadrant demodulator and counter 155, as illustrated in greater detail with respect to FIGS. 2A and 2B.

Figure 2A:
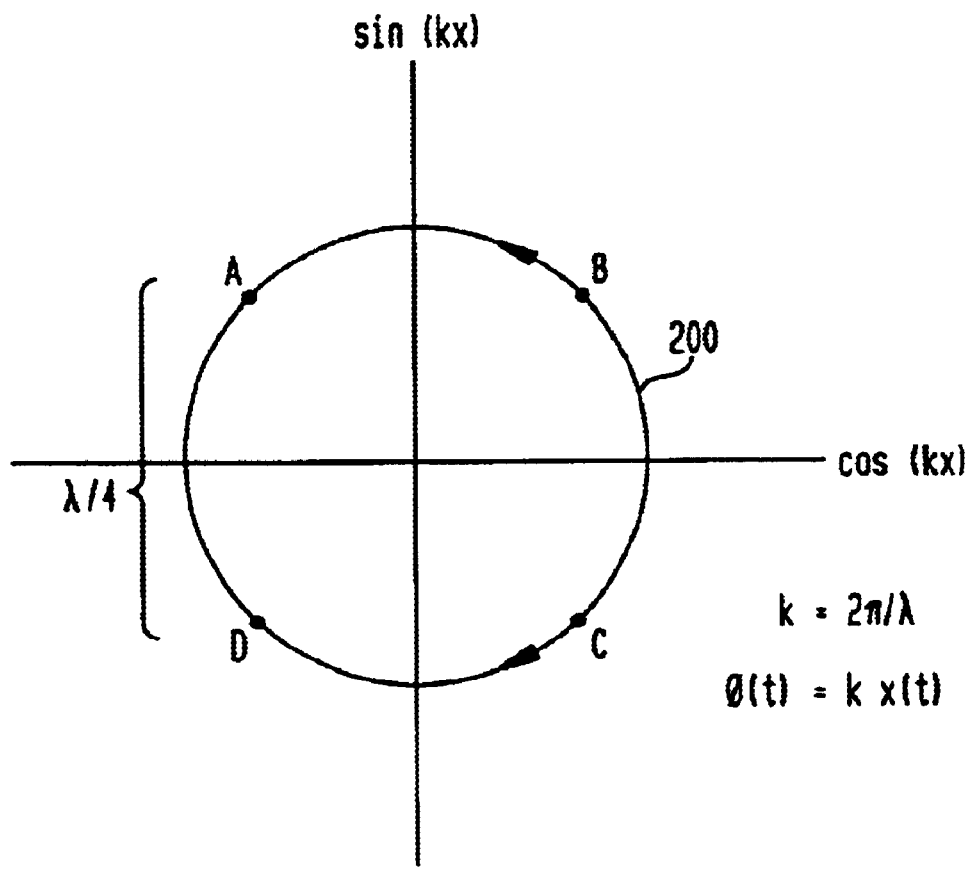
FIG. 2A is a graphical diagram illustrating phase transitions of an RF signal.
Figure 2B:
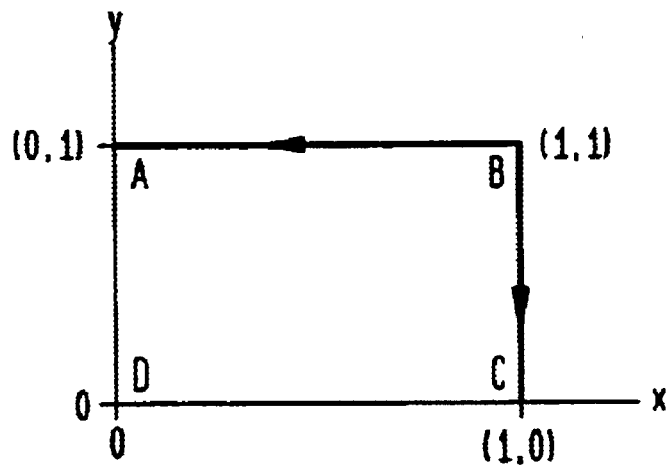
FIG. 2B is a graphical diagram illustrating digital phase transitions of an RF signal.

FIG. 2A is a graphical diagram illustrating phase transitions of the RF signal from detector 135. These phase transitions $\phi(t)$ are proportional to subject movement $x(t)$, i.e., $\phi(t) = k \; x(t)$, where $k = 2\pi/\lambda$. During quadrant demodulation, a point representative of the sine and cosine functions of the RF phase transitions will move (transition) either clockwise or counterclockwise in a circle 200, corresponding to the movement of the subject 150, with the circumference of the circle 200 equal to one wavelength. These phase transitions, in increments of one-quarter wavelength ($\lambda/4$), are digitized as unit pulses, as illustrated in FIG. 2B. For example, (clockwise) transitions from point A to point B, from point B to point C, from point C to point D, or from point D to point A, each correspond to one positive (or up) transition or pulse, with all such transitions counted and accumulated. Similarly, (counterclockwise) transitions from point A to point D, from point D to point C, from point C to point B, or from point B to point A, each correspond to one negative (or down) transition or pulse, with all such transitions counted and accumulated.

Referring again to FIG. 1, these various accumulated counts (positive (or up) or negative (or down) counts), as a displacement signal, are output from the quadrant demodulator and counter 155, and represent any movement of the subject 150 as measured by phase changes of the RF signal from the detector 135. The displacement signal output from the quadrant demodulator and counter 155 is converted to analog form in digital to analog converter 166, and also may be amplified in amplifier 170, to form a control voltage input into the manipulator arm 120. As a consequence, the control voltage input into the manipulator arm 120 is proportional to the displacement, during any given sampling interval, of the subject 150, and may be utilized to actively stabilize the probe 110 relative to such movement.

As indicated above, each count corresponds to subject movement in increments of one-quarter wavelength ($\lambda/4$). In the preferred embodiment, with a wavelength of 633 nm, each available increment for probe stabilization is approximately 0.15 microns, providing the capability for significant resolution for tracking subject movement. Also in the preferred embodiment, spontaneous subject movement resulted in displacement signals of up to thirty to forty microns without a loss of probe measurement capability. As a consequence, the system 100 of the present invention may provide active probe stabilization for comparatively large-scale or gross subject movements.

Continuing to refer to FIG. 1, in addition to or in lieu of being comprised of discrete components, the demodulator 140 may include a single integrated circuit ("IC"), or may include a plurality of integrated circuits or other components connected, arranged or grouped together, such as microprocessors, digital signal processors ("DSPs"), application specific integrated circuits ("ASICs"), associated memory (such as RAM and ROM), and other ICs and components. As a consequence, as used herein, the term demodulator or processor should be understood to equivalently mean and include a single processor, or arrangement of processors, microprocessors, controllers, or some other grouping of integrated circuits which perform the functions discussed above and also discussed below with reference to FIG. 3, with associated memory, such as microprocessor memory or additional RAM, ROM, EPROM or E$^2$PROM. The methodology of the invention, as discussed above and as discussed below with reference to FIG. 3, may be programmed and stored, in the demodulator 140 with its associated memory and other equivalent components, as a set of program instructions for subsequent execution when the demodulator 140 is operative (i.e., powered on and functioning).

FIG. 3 is a flow diagram illustrating a preferred method for interferometric probe stabilization relative to subject movement in accordance with the present invention. Beginning with start step 300, a probe is inserted into a prepared subject, step 305, such as inserting the probe 110 into the brain tissue of the subject 150. Subject preparation may include, for example, attachment of the reflector 121 in close proximity to the probe location, attachment of various monitors, and other antecedent surgical and sterilization procedures for the selected probe measurements. Next, in step 310, a light beam is transmitted to a reflector mounted on the subject, and a reflected light beam is received. A light beam (such as from the splitter 132) is modulated with an RF signal to form a reference beam, step 315. The reflected light beam and the reference beam are combined to form an interference pattern (or fringes), step 320.

Next, in step 325, the phase of the RF component of the interference pattern (or fringe) is detected, preferably using quadrature demodulation, to determine a displacement signal representing a direction and amount of subject movement, as discussed above. The displacement signal is then converted to analog to form the control voltage, step 330. The probe is then moved within the subject in response to the control voltage, step 335, desired probe measurements are made, step 340, and the method may end, return step 345.

Numerous advantages of the present invention may be apparent from the above discussion. The method and system of the present invention provide for probe stabilization, relative to subject movement, for accurate measurement within a live subject. The probe stabilization of the present invention is active, accommodating comparatively large-scale or gross subject movement which may otherwise interfere with accurate measurements. In addition, the method and system of the present invention do not alter or interfere with the physiological states of the subject, and otherwise minimizes contact with the subject tissue, to avoid interfering with the processes under study, to avoid tissue damage, and also to avoid other potential sources of error.

From the foregoing, it will be observed that numerous variations and modifications may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

What is claimed is:

1. A method for active probe stabilization, the probe stabilization relative to movement of a subject, the method comprising:
   (a) inserting a probe into the subject, the probe moveable in response to a control voltage;
   (b) transmitting a first light beam to the subject and receiving a reflected light beam;
   (c) modulating a second light beam with a modulating signal to form a reference light beam;
   (d) combining the reflected light beam and the reference beam to form an interference pattern;
   (e) detecting the interference pattern to determine a displacement signal;
   (f) converting the displacement signal to the control voltage, the displacement signal proportional to an amount and direction of subject movement; and (g) moving the probe within the subject in response to the control voltage.

2. The method of claim 1, further comprising:

(h) performing probe measurements within the subject.

3. The method of claim 1, wherein the modulating signal is a radio frequency signal.

4. The method of claim 1, wherein step (e) further comprises:

quadrature demodulating a phase component of the interference pattern to determine the displacement signal.

5. The method of claim 4, wherein the phase component is a phase shift of the radio frequency signal.

6. The method of claim 1, further comprising: splitting a laser light beam to form the first light beam and the second light beam.

7. The method of claim 1, wherein the displacement signal corresponds to an increment of subject movement of one fourth of a wavelength ($\lambda/4$) of the first light beam.

8. The method of claim 1, wherein probe movement in response to the control voltage is in a direction of the probe axis.

9. The method of claim 1, wherein probe movement in a direction lateral to the probe axis is passive.

10. The method of claim 1, wherein the probe is a microelectrode.

11. The method of claim 1, wherein the probe is a microscopic instrument.

12. The method of claim 1, wherein the probe is a surgical instrument.

13. The method of claim 1, wherein the probe is a fiber-optic scope.

14. The method of claim 1, wherein the probe is a microscope.

15. A system for active probe stabilization, the probe stabilization relative to movement of a subject, the system comprising:

a manipulator, the manipulator couplable to a probe, the probe being insertable into the subject, the manipulator operable to move the probe within the subject in response to a control voltage;

an interferometer, the interferometer operable to transmit a first light beam to the subject and to receive a reflected light beam; the interferometer further operative to modulate a second light beam with a modulating signal to form a reference light beam and to combine the reflected light beam and the reference beam to form an interference pattern;

a demodulator coupled to the manipulator and to the interferometer, the demodulator operable to detect the interference pattern to determine a displacement signal, the displacement signal proportional to an amount and direction of subject movement, and to convert the displacement signal to the control voltage.

16. The system of claim 15, wherein the modulating signal is a radio frequency signal.

17. The system of claim 16, wherein the demodulator is further operable to quadrature demodulate a phase component of the interference pattern to determine the displacement signal.

18. The system of claim 17, wherein the phase component is a phase shift of the radio frequency signal.

19. The system of claim 15, wherein the interferometer is further operable to split a laser light beam to form the first light beam and the second light beam.

20. The system of claim 15, wherein the displacement signal corresponds to an increment of subject movement of one fourth of a wavelength ($\lambda/4$) of the first light beam.

21. The system of claim 15, wherein probe movement in response to the control voltage is in a direction of the probe axis.

22. The system of claim 15, wherein probe movement in a direction lateral to the probe axis is passive.

23. The system of claim 15, wherein the probe is a microelectrode.

24. The system of claim 15, wherein the probe is a microscopic instrument.

25. The system of claim 15, wherein the probe is a surgical instrument.

26. The system of claim 15, wherein the probe is a fiber-optic scope.

27. The system of claim 15, wherein the probe is a microscope.

28. A system for active probe stabilization, the probe stabilization relative to movement of a subject, the system comprising:

a manipulator, the manipulator couplable to a probe, the probe being insertable into the subject, the manipulator operable to move the probe within the subject, in response to a control voltage, in a direction of the probe axis;

an interferometer, the interferometer operable to split a laser light beam to form a first light beam and a second light beam, to transmit the first light beam to the subject and to receive a reflected light beam; the interferometer further operative to modulate the second light beam with a radio frequency signal to form a reference light beam and to combine the reflected light beam and the reference beam to form an interference pattern;

a processor coupled to the manipulator and to the interferometer, wherein the processor includes instructions to quadrature demodulate a phase shift of a radio frequency component of the interference pattern to determine a displacement signal, the displacement signal proportional to an amount and direction of subject movement, and to convert the displacement signal to the control voltage.

* * * * *